United States Patent
Samuel et al.

(10) Patent No.: US 9,976,416 B2
(45) Date of Patent: May 22, 2018

(54) CASING WEAR ESTIMATION

(71) Applicant: Landmark Graphics Corporation, Houston, TX (US)

(72) Inventors: Robello Samuel, Cypress, TX (US); Aniket, Stafford, TX (US)

(73) Assignee: LANDMARK GRAPHICS CORPORATION, Houston, TX (US)

( * ) Notice: Subject to any disclaimer, the term of this patent is extended or adjusted under 35 U.S.C. 154(b) by 799 days.

(21) Appl. No.: 14/355,436

(22) PCT Filed: Jun. 25, 2013

(86) PCT No.: PCT/US2013/047592
§ 371 (c)(1),
(2) Date: Apr. 30, 2014

(87) PCT Pub. No.: WO2014/209282
PCT Pub. Date: Dec. 31, 2014

(65) Prior Publication Data
US 2015/0176401 A1  Jun. 25, 2015

(51) Int. Cl.
*E21B 49/00* (2006.01)
*G01N 29/04* (2006.01)
*E21B 44/00* (2006.01)
*E21B 47/00* (2012.01)

(52) U.S. Cl.
CPC ............ *E21B 49/003* (2013.01); *E21B 44/00* (2013.01); *E21B 47/00* (2013.01); *G01N 29/04* (2013.01)

(58) Field of Classification Search
CPC ........ E21B 49/003; E21B 44/00; E21B 47/00; G01N 29/04
See application file for complete search history.

(56) References Cited

U.S. PATENT DOCUMENTS

| | | |
|---|---|---|
| 3,682,256 A | 8/1972 | Stuart |
| 4,450,354 A | 5/1984 | Smith, Jr. et al. |
| 4,744,030 A | 5/1988 | Carlson et al. |
| 2002/0144545 A1 | 10/2002 | Cesmat et al. |
| 2004/0239316 A1 | 12/2004 | Yoo |
| 2006/0162962 A1* | 7/2006 | Koederitz ............. E21B 49/003 175/27 |
| 2012/0080184 A1 | 4/2012 | Jahangir et al. |

(Continued)

OTHER PUBLICATIONS

PCT Search Report and Written Opinion, PCT Application No. PCT/US2013/047592, dated Mar. 18, 2014.
(Continued)

*Primary Examiner* — Mohamed Charioui
*Assistant Examiner* — Jeremy Delozier

(57) ABSTRACT

Casing wear estimation. At least some of the illustrative embodiments are methods including: calculating a value indicative of static casing wear of the drilling operation, the static casing wear caused by interaction of a drill string against an inside diameter of a casing; calculating a value indicative of impact casing wear of the drilling operation, the impact casing wear caused by interaction of the drill string against the inside diameter of a casing; and combining the value indicative of static casing wear and the value indicative of impact casing wear to determine the value indicative of aggregate casing wear.

17 Claims, 11 Drawing Sheets

(56) References Cited

U.S. PATENT DOCUMENTS

2012/0123757 A1* 5/2012 Ertas .................. E21B 45/00
703/2

OTHER PUBLICATIONS

Intellectual Property Office of Singapore, Written Opinion, Application No. 11201510071Y, dated Jun. 9, 2016, 8 pages, Singapore.
Steven Ripman, Casing wear in multilateral weils. Master's Thesis (University of Stavanger), Jun. 15, 2011, p. 9, 12, 36, 61 and 66.
European Patent Office, Supplementary European Search Report and Written Opinion, dated Nov. 21, 2016, 11 pages, Europe.
R.W. Hall, Jr., Ali Garkasi, Greg Deskins and John Vozniak, Recent Advances in Casing Wear Technology, Feb. 15-18, 1994, 8 pages, SPE/IADC Drilling Conference, SPE 27532, Society of Petroleum Engineers, Dallas, TX.
J. Steve Williamson, Casing Wear: The Effect of Contact Pressure, Oct. 5-7, 1981, 7 pages, SPE-10236, Society of Petroleum Engineers, SPE 56th Annual Technical Conference and Exhibition, San Antonio, TX.
Bruno Best, Casing Wear Caused by Tooljoint Hardfacing, Oct. 5-8, 1983, 9 pages, SPE 11992, 1983 SPE Annual Technical Conference and Exhibition, Society of Petroleum, San Francisco, CA.
Sarah Mitchell and Yanghua Xiang, Improving Casing Wear Prediction and Mitigation Using a Statistically Based Model, Mar. 6-8, 2012, 15 pages, 2012 IADC/SPE Drilling Conference and Exhibition, SPE 151448, San Diego, California.
Russell W. Hall, Jr., and Kenneth P. Malloy Sr., Contact Pressure Threshold: An Important New Aspect of Casing Wear, Apr. 17-19, 2005, 7 pages, 2005 SPE Production and Operations Symposium, SPE 94300, Society of Petroleum Engineers, Oklahoma, City, OK.
Jerry P. White and Rapier Dawson, Casing Wear: Laboratory Measurements and Field Predictions, Sep. 22-25, 1985, 7 pages, 1985 SPE Annual Technical Conference and Exhibition, SPE 14325, Society of Petroleum Engineers, Las Vegas.
N.B. Moore, P.W. Mock and R.E. Krueger, Reduction of Drill String Torque and Casing Wear in Extended Reach Wells Using Non-Rotating Drill Pipe Protectors, May 22-24, 1996, SPE 35666, Western Regional Meeting, Society of Petroleum Engineers, Anchorage, Alaska.

* cited by examiner

PARABOLIC

ELLIPTICAL

COSINE

POSITIVELY SKEWED

US 9,976,416 B2

CASING WEAR ESTIMATION

BACKGROUND

In the drilling of wellbores for hydrocarbon exploration and production, a portion of the wellbore will be drilled and cased with a casing, and thereafter the length of wellbore will be extended by further drilling. During the further drilling, the drill string extends through and contacts the casing, which contact by the drill string may cause casing wear. Casing wear may be particularly pronounced in deviated portions of the wellbore (i.e., those portions of the wellbore that are not vertically orientated). Although some casing wear is expected, excess casing wear can adversely affect both structural integrity of a wellbore as well as the casing's ability to withstand exposure to high pressures within the casing (e.g., during hydraulic fracturing, and formation pressure).

As the length and geometrical complexity of wellbores increase with improved drilling technology, existing casing wear models cannot accurately predict casing wear.

BRIEF DESCRIPTION OF THE DRAWINGS

For a detailed description of exemplary embodiments, reference will now be made to the accompanying drawings in which.

NOTATION AND NOMENCLATURE

Figure 1:
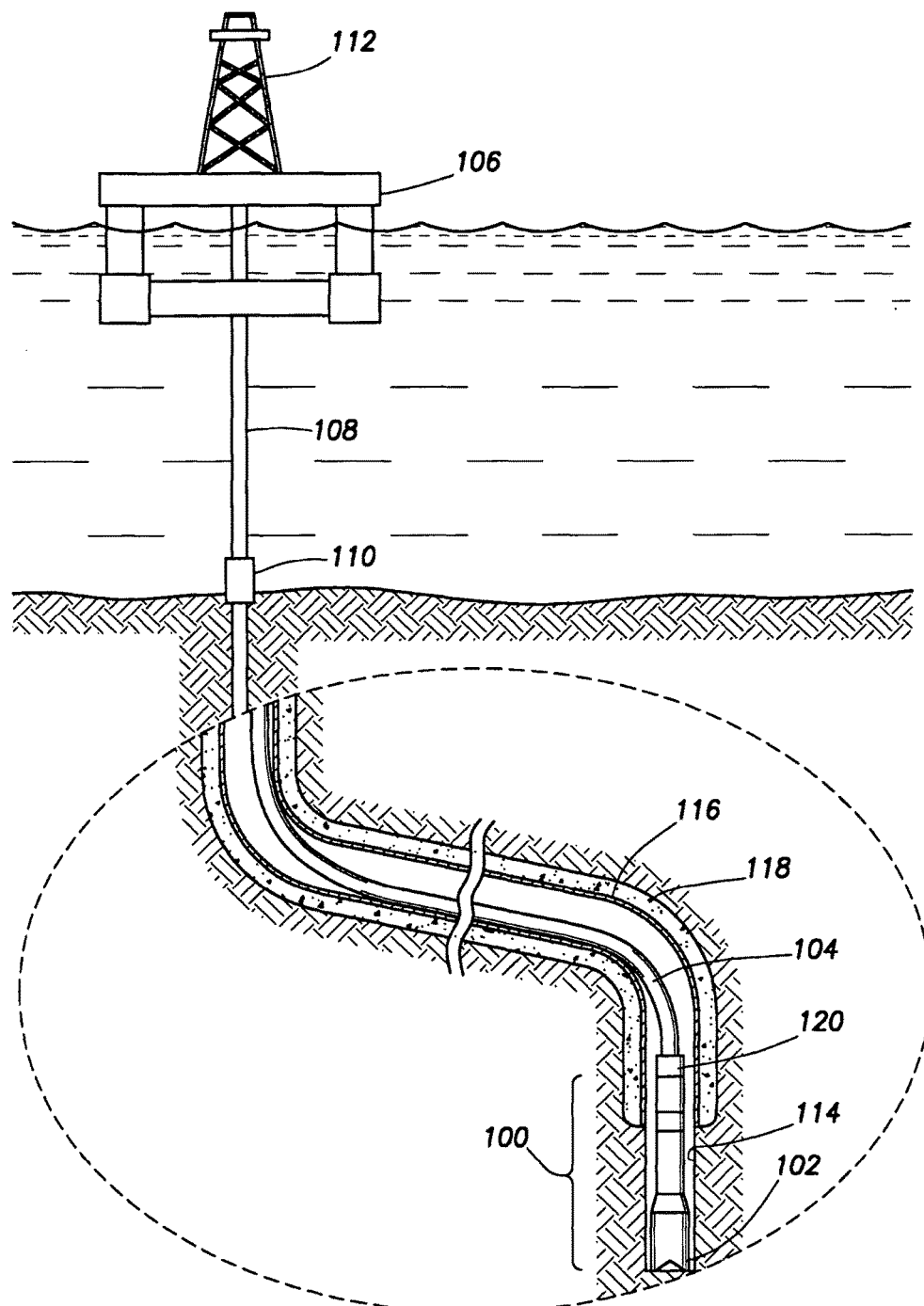
FIG. 1 is a side elevation, partial cross-sectional, view that shows an operational environment in accordance with at least some embodiments.

Certain terms are used throughout the following description and claims to refer to particular system components. As one skilled in the art will appreciate, different companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Static casing wear" shall mean casing wear caused by contact between an outside surface of a drill string and an inside diameter of a casing where the contact is continuous over at least one revolution of the drill string.

"Impact casing wear" shall mean casing wear caused by an outside surface of a drill string periodically striking an inside diameter of a casing, where the frequency of the striking is a function of rotational speed of the drill string. Changes in normal force at a contact point between the outside surface of a drill string and an inside diameter of the casing, where the change in normal force does not result in physical separation, shall not be considered to result in impact casing wear.

"Sinusoidal", in reference to cross-sectional wear patterns, shall mean a wear pattern having a sine- or cosine-based distribution.

"Real-time" in reference to data associated with a drilling operation shall mean data created within five minutes of an event or action, or data received within five minutes of creation of the data.

ORGANIZATIONAL SUMMARY

The specification is organized as a plurality of sections and subsections. The following outline of the sections and subsections is provided to assist the reader in understanding the organizational structure of the document.
Example Operational Environments
Casing Wear Modes and Models
Static Casing Wear
Impact Casing Wear
  Parabolic Model
  Elliptical Model
  Cosine Model
  Positively Skewed
Aggregate Casing Wear
Vibration and Force Magnitudes
Software-based Determinations
Measured Vibration
Adjusting the Model
Example Computing Environment

DETAILED DESCRIPTION

The following discussion is directed to various embodiments of the invention. Although one or more of these embodiments may be preferred, the embodiments disclosed should not be interpreted, or otherwise used, as limiting the scope of the disclosure and claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various example methods and systems are directed to determining a value of aggregate casing wear. In particular, example methods and systems combine a static casing wear component and an impact casing wear component to arrive at the value of aggregate casing wear. The static casing wear component may be considered to be that portion of the casing wear caused by "continuous" contact of a portion of the drill string against an inside diameter of a casing. As an example, static casing wear may occur within a long horizontal section of the wellbore where the force of gravity causes the drill string to abut a lower portion of the casing. The impact casing wear component may be considered to be the portion of the casing wear caused by repetitive striking of the drill string against the inside diameter of the casing. As an example, impact casing wear may occur near the distal end of the drill string where rotational imbalances cause portions of the bottomhole assembly to repetitively strike the casing during rotation of the drill string. The specification first turns to a description of illustrative drilling systems, and then provides a more detailed explanation of operation of various embodiments within the illustrative systems.

Example Operational Environments

FIG. 1 shows an example subsea drilling operation. In particular, FIG. 1 shows a bottomhole assembly 100 for a subsea drilling operation, where the bottomhole assembly 100 illustratively comprises a drill bit 102 on the distal end of the drill string 104. Various logging-while-drilling (LWD) and measuring-while-drilling (MWD) tools may also be coupled within the bottomhole assembly 100. The drill string 104 (including the bottomhole assembly 100) is lowered from a drilling platform 106. The drill string 104 extends through a riser 108 and a well head 110. Drilling equipment supported within and around derrick 112 (illustrative drilling equipment discussed in greater detail with respect to FIG. 2) may rotate the drill string 104, and the rotational motion of the drill string 104 forms the borehole 114. In the example of FIG. 1, the drill string 104 extends through a casing string 116 illustratively held in place, at least in part, by cement 118. In the example shown the borehole 114 extends beyond the distal end of the casing 116.

In accordance with at least some embodiments, the bottomhole assembly 100 may further comprise a communication subsystem. In particular, illustrative bottomhole assembly 100 comprises a telemetry module 120. Telemetry module 120 may communicatively couple to various LWD and/or MWD tools in the bottomhole assembly 100 and receive data measured and/or recorded by the tools. The telemetry module 120 may communicate logging data to the surface using any suitable communication channel (e.g., pressure pulses within the drilling fluid flowing in the drill string 104, acoustic telemetry through the pipes of the drill string 104, electromagnetic telemetry, optical fibers embedded in the drill string 104, or combinations), and likewise the telemetry module 124 may receive information from the surface over one or more of the communication channels.

Figure 2:
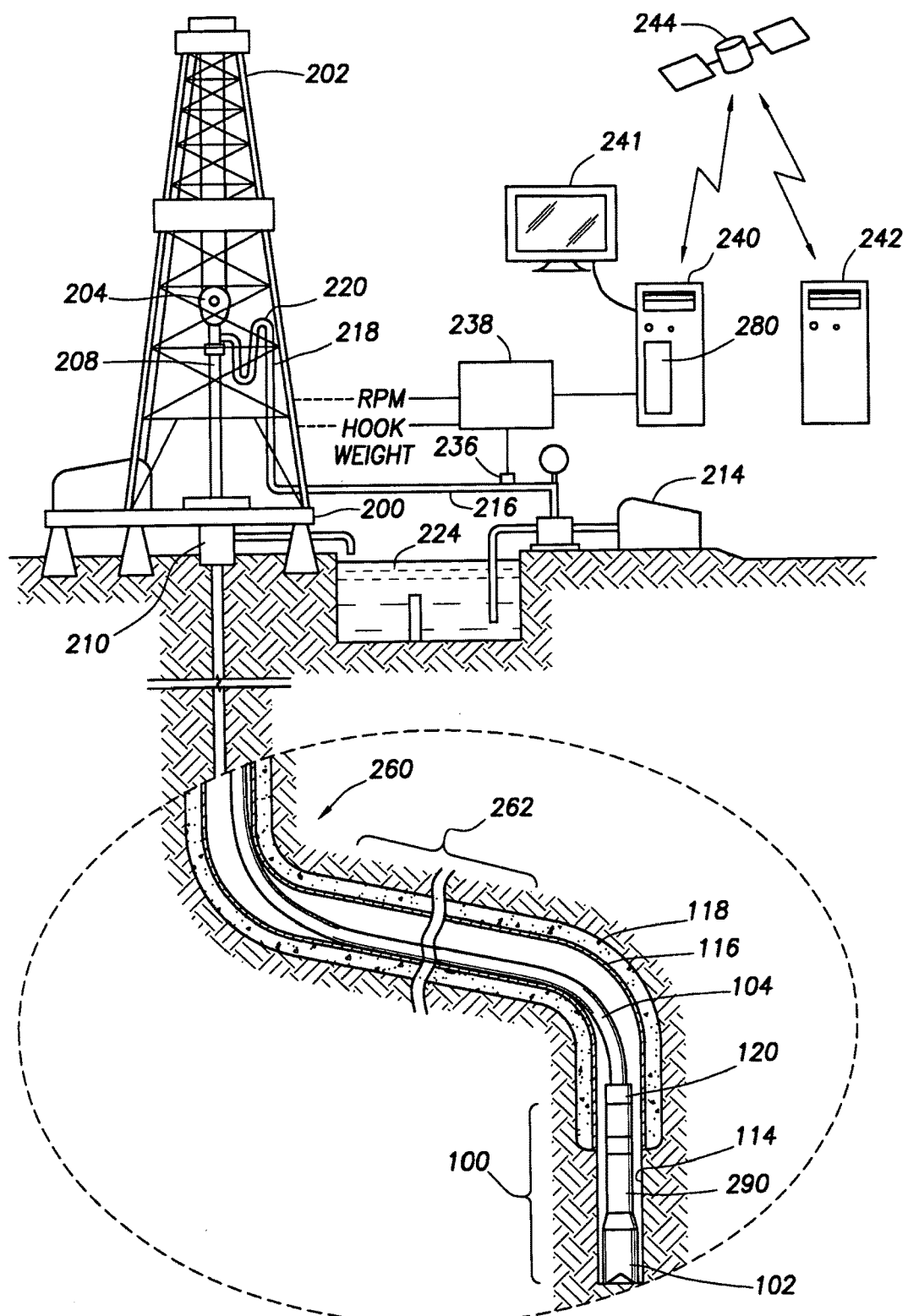
FIG. 2 is a side elevation, partial cross-sectional, view that shows another operational environment in accordance with at least some embodiments.

FIG. 2 shows an example land-based drilling operation. In particular, FIG. 2 shows a drilling platform 200 equipped with a derrick 202 that supports a hoist 204. The hoist 204 suspends a top drive 208, and the hoist 204 and top drive rotate and lower the drill string 104 through the wellhead 210. Drilling fluid is pumped by mud pump 214 through flow line 216, stand pipe 218, goose neck 220, top drive 208, and down through the drill string 104 at high pressures and volumes to emerge through nozzles or jets in the drill bit 102. The drilling fluid then travels back up the wellbore via the annulus, through a blowout preventer (not specifically shown), and into a mud pit 224 on the surface. On the surface, the drilling fluid is cleaned and then circulated again by mud pump 214. The drilling fluid is used to cool the drill bit 102, to carry cuttings from the base of the borehole to the surface, and to balance the hydrostatic pressure in the rock formations.

In the illustrative case of the telemetry model 120 encoding data in pressure pulses that propagate to the surface by way of the drilling fluid in the drill string 104, transducer 236 converts the pressure signal into electrical signals for a signal digitizer 238 (e.g., an analog-to-digital converter). The digitizer 238 supplies a digital form of the pressure signals to a surface computer 240 or some other form of a data processing device. Surface computer 240 operates in accordance with software (which may be stored on a computer-readable storage medium) to monitor and control the drilling processing, including instructions to calculate or estimate casing wear (discussed more thoroughly below). The surface computer 240 is further communicatively coupled to many devices in and around the drilling site by way of digitizer 238, such as indications of the rotational speed (revolutions per minute (RPM)) of the drill string 104 as turned by the top drive 208, and hook weight (related to weight-on-bit) as measured by devices associated with the hoist 204.

In some cases, the casing wear estimations of the example embodiments may be displayed on a display device 241. In yet still other example embodiments, the surface computer 240 may forward gathered data to another computer system, such as a computer system 242 at the operations center of the oilfield services provider, the operations center remote from the drill site. The communication of data between computer system 240 and computer system 242 may take any suitable form, such as over the Internet, by way of a local or wide area network, or as illustrated over a satellite 244 link. Some or all of the calculations associated with aggregate casing wear may be performed at the computer system 242, and relayed back to the surface computer 240 and display device 241.

In example systems, a value of aggregate casing wear provided to the driller may result in the driller making changes to drilling parameters associated with the drilling process. That is, when excess casing wear is predicted for a portion of the casing 116, the driller may make changes such as changing the rotational speed of the drill string, changing the weight-on-bit, and/or tripping the drill string (i.e., removing the drill string from the casing 116) and changing a component of the bottom hole assembly and/or the drill string. For example, a portion of the bottomhole assembly 100 may be removed to change rotational vibration characteristics, or to shorten/lengthen the bottomhole assembly 100. A shorter or longer bottomhole assembly 100 may relocate the contact point of tools joints (discussed more below) in the drill string against the inside diameter of the casing 116.

Casing Wear Modes and Models

Figure 3B:
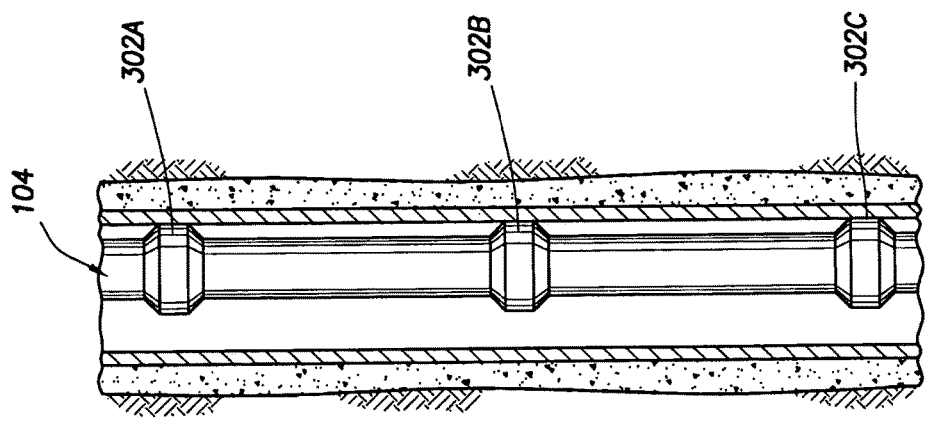
FIG. 3B is a side elevation, partial cross-sectional, view that shows a view of drill string within a wellbore.
Figure 3A:
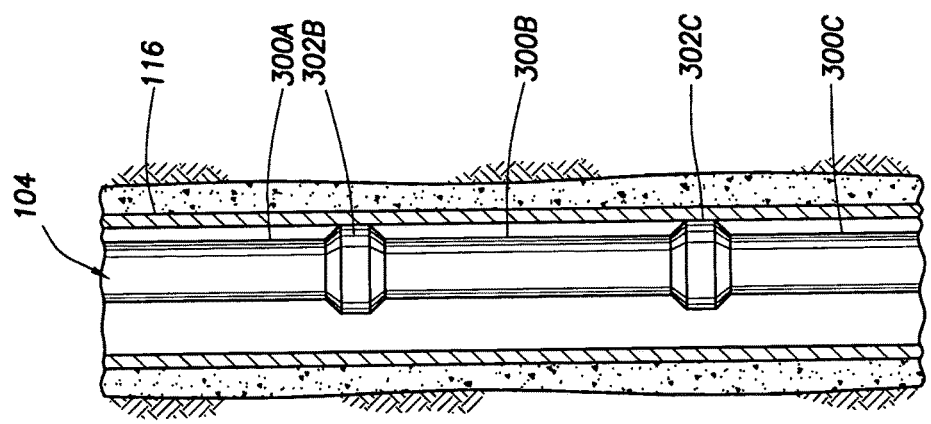
FIG. 3A is a side elevation, partial cross-sectional, view that shows a view of drill string within a wellbore.

The specification now turns to an explanation of various casing wear modes, the discussion in reference to FIGS. 2 and 3A-B. It is noted, however, that FIG. 2 is simplified for purposes of explanation, and the relative sizes of the various components are not drawn to scale. For example, in actual drilling the turning radius for changes in direction may be on the order 1000 feet or more, and thus the bends in the example wellbore of FIG. 2 are not shown to scale. As another example, the relative sizes of the drill string 104 and casing 116 are exaggerated to convey certain concepts related to casing wear modes contemplated by the various embodiments.

Moreover, the drill string 104, though shown as continuous, actually comprises a series of pipe sections (e.g., 30 foot sections, or 40 foot sections) coupled together piece-by-piece as the drill string is lowered into the borehole. The pipe sections that create the overall drill string have threads on each end—one male or "pin" end with external threads and one female or "box" end with internal threads. The pin end of one drill pipe couples to the box end of the next drill pipe. In many cases, particularly cases of small outside diameter drill pipe, the box end of the pipe defines a larger cross-sectional area (i.e., has a larger diameter) than, for example, in the middle of the pipe section. Moreover, the larger diameter associated with the box end may be hardened or have a protective coating, which protective coating reduces wear on the pipe section but may accelerate casing wear. The larger diameter portions of the drill pipe may be referred to as "tool joints" in the industry.

FIGS. 3A and 3B show elevation, partial cross-section, views of a portion of the drill string 104 in a cased portion of a wellbore, along with tool joints. In particular, FIG. 3A shows a portion of the drill string 104 where three example pipe sections 300A-C are visible. The drill string 104 is disposed within the casing 116, and also visible is the example cement. The drill string 104 comprises a series of tool joints, where tool joints 302B and 302C are visible in FIG. 3A. Casing wear is caused predominantly by the larger diameter tool joints 302 interacting with the inside diameter of the casing 116, and as drilling continues the location of a tool joint 302 in relation to the casing changes. For example, FIG. 3B shows the system of FIG. 3A, but where the drilling has advanced downward, thus causing the location of the tool joints 302B and 302C to move downward (as well as to make tool joint 302A visible).

In accordance with example methods and systems, the casing wear determinations are made with respect to the location of interaction of the tool joints 302 against the casing, as well as interaction of the bottomhole assembly 400 against the casing (when the bottomhole assembly is located inside the casing). Thus, casing wear at any particular location in the casing may be created by a plurality of tool joints creating wear based on rotation of the tool joint against and/or striking the casing, each tool joint passing the particular location at a particular time as the drill string translates within the casing. It follows that the casing can be conceptually divided into a plurality of sections or intervals, and the casing wear within each interval estimated and tracked. In some cases, the interval length for estimating and tracking casing wear may be one foot in length (e.g., the first interval extending from the surface down one foot of casing length, the second interval abutting the first interval and spanning the next foot of casing length, and interval N being N feet from the surface along the casing and spanning one foot of casing length). However, longer and shorter intervals are also contemplated, as are intervals of differing length. For example, areas where little casing wear is expected (e.g., vertical portions) can be lumped into longer intervals, but areas where higher casing wear is expected (e.g., bends, long horizontal sections) can have shorter intervals.

Before proceeding, it is noted that the various embodiments were developed in the context of casing wear at respective tool joint and bottomhole assembly locations, and the balance of the specification is based on the developmental context. However, casing wear may be caused by any portion of a drill pipe (e.g., the middle between two tool joints) and, with the dedication of sufficient computing resources, casing wear caused by any portion of a drill string 104 may be estimated and tracked. With the caveats regarding the drawings in mind, as well as the issue regarding tool joints, the first casing wear mode discussed is static casing wear.

Static Casing Wear

Returning briefly to FIG. 2, FIG. 2 illustrates certain locations where the drill sting 104 may contact the inside diameter of the casing 116. In particular, at bend 260 the drill string is shown to contact the inside radius of the casing. The contact at bend 260 may be held in place by torque on the drill string, the torque in this case caused by the drill string extending through the bend (as opposed to rotational torque imparted by the top drive assembly 208). As the drill string 104 is rotated by the top drive assembly 208, the portion of the drill string abutting and turning against the casing at the bend 260 may result in "static casing wear" in the absence of significant vibration. That is, the portion of the drill string at the bend 260 abuts the inside diameter of the casing for multiple revolutions of the drill string 104 and thus makes contact for an extended period of time (relative to impact casing wear, discussed more below). In the situation of bend 260, the normal force between the portion of the drill string and the bend 260 may be perpendicular to the location of physical contact, and it follows that in this example the normal force is not aligned with gravity.

Likewise, in the long, relatively straight section 262, the drill string 104 may be held against the lower portion of the casing 116 by the force of gravity. Thus, in this case of the straight section 262 the normal force and gravity may be at least partially aligned. As the drill string 104 is rotated by the top drive assembly 208, the portion of the drill string abutting and turning against the casing on the lower portion of the straight section 262 may result in static casing wear along that section.

Figure 4:
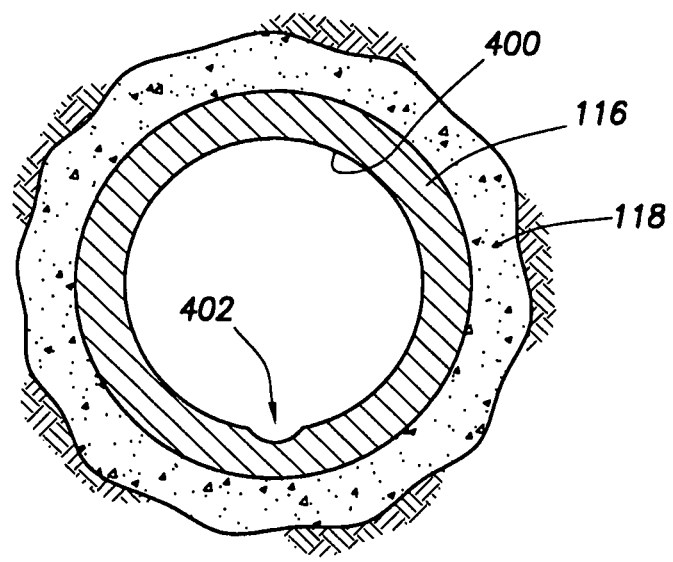
FIG. 4 is a cross-sectional end elevation view of a wellbore that shows example static casing wear in accordance with at least some embodiments.

FIG. 4 shows a cross-sectional end elevation view of a portion of the casing where static casing wear has taken place. In particular, FIG. 4 shows the casing 116 with the cement 118 disposed between the casing 116 and the formation. The casing 116 defines an internal diameter 400. In the example of FIG. 4, the static casing wear 402 is present in the "bottom" of the casing 116, such as might be the case in the straight section 262 where the force of gravity holds the drill string against the lower portion of the casing. It will be understood, however, that the location of the static casing wear is not limited to just the bottom portion of the casing, and in fact may occur at any location on the inside diameter of the casing 116. However, the locations of the interaction between the drill string 104 and the inside diameter of the casing are calculable and thus known based on the geometry of the wellbore.

In accordance with example systems, a value of static casing wear at any particular interval may be modeled based on the following equation:

$$V_{static} = WF * F_s * \pi * D_{tj} * N * 60 * T * f \tag{1}$$

where $V_{static}$ is the volume of casing wear at a particular interval of the casing, WF is the wear factor in square inches per pound (e.g., $5 \times 10^{-10}$), $F_s$ is side or normal force at the contact point in pounds force (e.g., 50), $D_{tj}$ is the outer diameter of the tool joint under consideration, N is the rotational speed of the drill string in RPM, T is the total static rotation time, and f is the ratio of the length of the tool joint to the length of the pipe.

Impact Casing Wear

In addition to the static casing wear mode, the casing may also experience casing wear associated with the rotational dynamics of the drill string. In particular, at certain rotational speeds the drill string 104 may experience vibration about the long axis of the drill string 104. Moreover, because a controlled weight is applied to the drill bit 102 to achieve controlled rate of penetration during drilling, the drill string 104 may be under compressional forces. The lack of rotational balance, alone or combination with the applied compressional force, may create vibrations in the drill string 104 when the rotational speed of the drill string approaches resonant frequencies (or harmonics thereof). For example, at particular rotational speeds the portion of the drill string 104 within the straight section 262 may experience vibration resulting in sufficient force (and orientation of the force) to momentarily lift a portion drill string 104 such that there is a lack of contact between the portion of the drill string 104 and the casing 116. As the vibratory force rotates around to be more aligned with the force of gravity (in this example), the portion of the drill string 104 may strike or impact the internal diameter of the casing 116. Likewise at the distal end of the drill string 104, and particularly the bottomhole assembly 100, the bottomhole assembly 100 may experience vibration resulting in sufficient force and orientation of the force to cause the bottomhole assembly 100 to periodically impact the casing 116. It is noted that the vibratory motion caused by rotation of the drill string 104 creating the impacts of the drill string 104 against the casing may take place simultaneously at multiple locations along the length of the overlap between drill string and casing. In the example situation of FIG. 2, impact caused by vibration of the drill string may simultaneously take place in the example bend 260, in the example straight section 262, and at the distal end by way of the bottomhole assembly 100.

The inventors of the current specification have found that the impacts of the drill string against the casing may result in multiple types of wear patterns having distinct features when considered in cross-section, and thus each wear pattern may result in a distinct model used to estimate the casing wear. Actual casing wear may be a combination of many wear patterns, and thus estimating the casing wear may be based on a combination of the wear models. The first casing wear type and model is referred to as the parabolic model.

Parabolic Model

Figure 5:
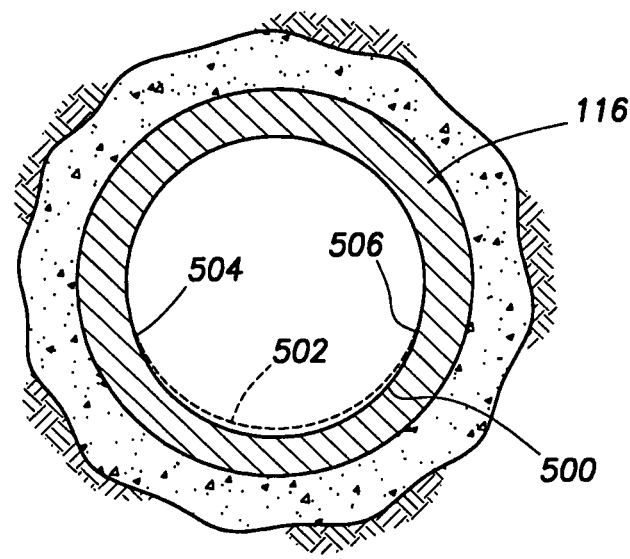
FIG. 5 is a cross-sectional end elevation view of a wellbore that shows example parabolic casing wear in accordance with at least some embodiments.

FIG. 5 shows a cross-sectional end elevation view of a portion of the casing having casing wearing with a parabolic cross-sectional wear pattern. In particular, FIG. 5 shows the example parabolic casing wear 500 present in the "bottom" of the casing 116, such as might be the case in the straight section 262. For reference, FIG. 5 shows the unworn casing as dashed line 502. It will be understood, however, that the location of the parabolic casing wear is not limited to just the bottom portion of the casing, and in fact may occur at any location on the inside diameter of the casing 116.

Although the inventors do not wish to be tied to any particular creation mechanism, one theory regarding creation of the parabolic casing wear 500 is a vibratory pattern where the tool joint (not shown) initially impacts the casing at location 504 and then "wipes" the inside diameter to location 506 before again being lifted from contact with the casing by the vibratory forces. During "wiping", the magnitude of the force between the tool joint and the inside diameter of the casing has parabolic distribution as a function of distance along the inside diameter. Other physical explanations are also possible, and a competing method or system that falls within the claims below shall not be considered to avoid infringement merely for framing the interaction with a different theory regarding the physical creation mechanism.

In accordance with example systems, a value of impact casing wear at any particular interval may be modeled on a per impact basis according to the following equation:

$$V_{impact} = \int_0^{t_i} \frac{k}{H}\left(\frac{N}{60}\right)\pi D_{ij} F(t) dt \qquad (2)$$

where $V_{impact}$ is the volume of casing wear for a single impact, $t_i$ is the total impact time, H is hardness of the casing (e.g., $1\times10^9$ Pascal), k is a dimensionless abrasive wear coefficient of the casing (e.g., $3\times10^{-4}$), N is the rotational speed of the drill string in RPM, $D_{tj}$ is the outer diameter of the tool joint under consideration, and F(t) is the magnitude of the force applied as a function of time t.

For the example parabolic force distribution and thus parabolic model, the magnitude of the force applied as a function of time may be modeled according to the following equation:

$$F(t) = F_{max}\left[1 - 4\left(\frac{t}{t_i} - \frac{1}{2}\right)^2\right] \qquad (3)$$

where again F(t) is the magnitude of the force applied as a function of time t, $F_{max}$ is the maximum impact force (e.g., 2000 Newtons), and again $t_i$ is the total impact time. In some cases $F_{max}$ is the same as $F_s$ for the static case, being the side or normal force at the contact point.

Thus, for the example parabolic casing wear, for each interval of the casing under consideration a value of impact casing wear (when present) having a parabolic cross-sectional wear pattern for each impact of the tool joint against the casing may be determined or modeled using Equation (2) based on the force as a function of time provided by Equation (3).

Elliptical Model

Figure 6:
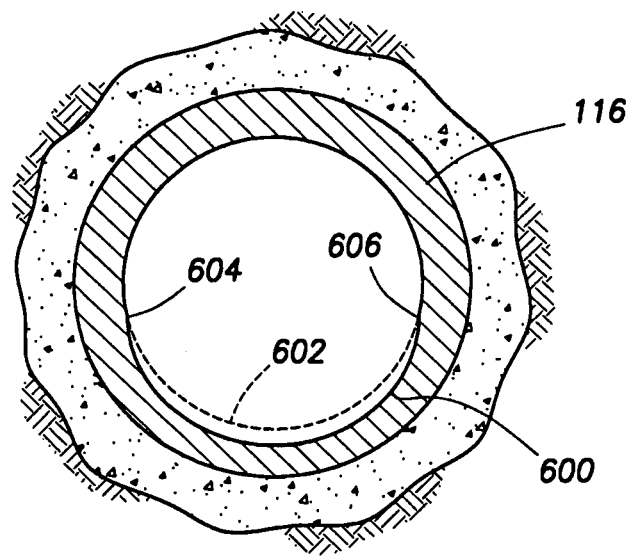
FIG. 6 is a cross-sectional end elevation view of a wellbore that shows example elliptical casing wear in accordance with at least some embodiments.

FIG. 6 shows a cross-sectional end elevation view of a portion of the casing having an elliptical cross-sectional wear pattern. In particular, FIG. 6 shows the example elliptical casing wear 600 present in the "bottom" of the casing 116, such as might be the case in the straight section 262. For reference, FIG. 6 shows the un-worn casing as dashed line 602. It will be understood, however, that the location of the elliptical casing wear is not limited to just the bottom portion of the casing, and in fact may occur at any location on the inside diameter of the casing 116.

Although the inventors do not wish to be tied to any particular creation mechanism, one theory regarding creation of the elliptical casing wear 600 is a vibratory pattern where the tool joint (not shown) initially impacts the casing at location 604 and then "wipes" the inside diameter to location 606 before again being lifted from contact with the casing by the vibratory forces. During "wiping", the magnitude of the force between the tool joint and the inside diameter of the casing has an elliptical distribution as a function of distance along the inside diameter. Other physical explanations are also possible, and a competing method or system that falls within the claims below shall not be considered to avoid infringement merely for framing the interaction with a different theory of the physical creation mechanism.

As before, a value of impact casing wear at any particular interval may be modeled on a per impact basis according to Equation (2) above. For the example elliptical force distribution and thus elliptical model, the magnitude of the force applied as a function of time may be modeled according to the following equation:

$$F(t) = F_{max}\sqrt{\left[1 - 4\left(\frac{t}{t_i} - \frac{1}{2}\right)^2\right]} \qquad (4)$$

where the variables are as defined with respect to Equation (3).

Thus, for the example elliptical casing wear, for each interval of the casing under consideration a value of impact casing wear (when present) having an elliptical cross-sectional wear pattern for each impact of the tool joint against the casing may be determined or modeled using Equation (2) based on the force as a function of time provided by Equation (4).

Cosine Model

Figure 7:
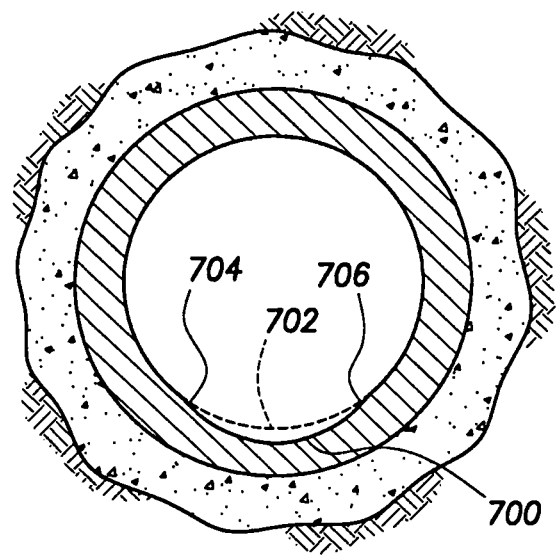
FIG. 7 is a cross-sectional end elevation view of a wellbore that shows example cosine casing wear in accordance with at least some embodiments.

FIG. 7 shows a cross-sectional end elevation view of a portion of the casing having cosine-based cross-sectional wear pattern. In particular, FIG. 7 shows the example cosine casing wear 700 present in the "bottom" of the casing 116, such as might be the case in the straight section 262. For reference, FIG. 7 shows the unworn casing as dashed line 702. It will be understood, however, that the location of the cosine casing wear is not limited to just the bottom portion of the casing, and in fact may occur at any location on the inside diameter of the casing 116.

Although the inventors do not wish to be tied to any particular creation mechanism, one theory regarding creation of the cosine casing wear 700 is a vibratory pattern where the tool joint (not shown) initially impacts the casing at location 704 and then "wipes" the inside diameter to location 706 before again being lifted from contact with the casing by the vibratory forces. During "wiping", the magnitude of the force between the tool joint and the inside diameter of the casing has a cosine-based distribution as a function of distance along the inside diameter. Other physical explanations are also possible, and a competing method or system that falls within the claims below shall not be considered to avoid infringement merely for framing the interaction with a different theory of the physical creation mechanism.

As before, a value of impact casing wear at any particular interval may be modeled on a per impact basis according to Equation (2) above. For the example cosine model, the magnitude of the force applied as a function of time may be modeled according to the following equation:

$$F(t) = \frac{F_{max}}{2}\left[1 + \cos\left(\frac{2\pi t}{t_i} - \pi\right)\right] \qquad (5)$$

where the variables are as defined with respect to Equation (3).

Thus, for the example cosine casing wear, for each interval of the casing under consideration a value of impact casing wear (when present) having a cosine-based cross-sectional wear pattern for each impact of the tool joint against the casing may be determined or modeled using Equation (2) based on the force as a function of time provided by Equation (5).

Positively Skewed

Figure 8:
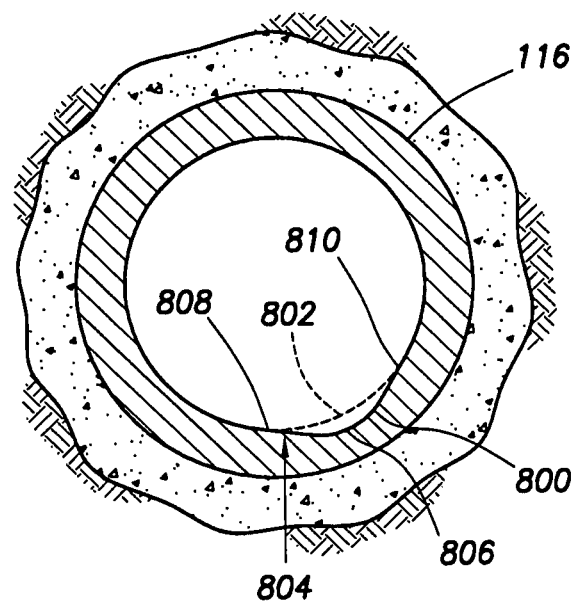
FIG. 8 is a cross-sectional end elevation view of a wellbore that shows example positively skewed casing wear in accordance with at least some embodiments.

FIG. 8 shows a cross-sectional end elevation view of a portion of the casing having a positively skewed cross-sectional wear pattern. In particular, FIG. 8 shows the example positively skewed casing wear 800 (i.e., having cross-sectional wear pattern where a single wear peak is offset radially from a static wear peak) present in the "bottom" of the casing 116, such as might be the case in the straight section 262. For reference, FIG. 8 shows the unworn casing as dashed line 802. Static casing wear in this example, though not shown, would be at location 804, and thus the peak 806 of the positively skewed casing wear is offset radially (i.e., at a different radial location on the inside diameter of the casing 116). It will be understood, however, that the location of the positively skewed casing wear is not limited to just the bottom portion of the casing, and in fact may occur at any location on the inside diameter of the casing 116.

Although the inventors do not wish to be tied to any particular theory of the creation mechanism, one theory regarding creation of the positively skewed casing wear 800 is a vibratory pattern where the tool joint (not shown) initially impacts the casing at location 808 and then "wipes" the inside diameter to location 810 before again being lifted from contact with the casing by the vibratory forces. During "wiping", the magnitude of the force between the tool joint and the inside diameter of the casing has a positively skewed distribution as a function of distance along the inside diameter. Other physical explanations are also possible, and a competing method or system that falls within the claims below shall not be considered to avoid infringement merely for framing the interaction with a different theory of the physical creation mechanism.

As before, a value of impact casing wear at any particular interval may be modeled on a per impact basis according to Equation (2) above. For the example positively skewed model, the magnitude of the force applied as a function of time may be modeled according to the following equation:

$$F(t) = \frac{F_{max}}{y_{max}}\left[\frac{2}{\omega}\varphi\left(\frac{x(t) - \xi}{\omega}\right)\Phi\left(\alpha\left(\frac{x(t) - \xi}{\omega}\right)\right)\right] \qquad (6)$$

where $F_{max}$ is as defined above, $y_{max}$ is a maximum y-axis value for the chosen skewed function, $\omega$ is a scale parameter for the skewed function, $\xi$ is a location parameter for the skewed function, and $\alpha$ is a shape parameter for the skewed function. The functions $x(t)$, $\varphi(x)$, and $\phi(x)$ are given below.

$$x(t) = x_{max}\frac{t}{t_i} \qquad (7)$$

where $x_{max}$ is a maximum x-axis value for the chosen skewed function, and t and $t_i$ are as defined above.

$$\varphi(x) = \frac{1}{\sqrt{2\pi}}e^{\frac{x^2}{2}} \qquad (8)$$

and $$\Phi(x) = \frac{1}{2}\left[1 + \mathrm{erf}\left(\frac{x}{\sqrt{2}}\right)\right] \quad (9)$$

where erf is an error function (i.e., the Gauss error function).

Thus, for the example positive skewed casing wear, for each interval of the casing under consideration a value of impact casing wear (when present) having a positively skewed cross-sectional wear pattern for each impact of the tool joint against the casing may be determined or modeled using Equation (2) based on the force as a function of time provided by Equation (6) and related Equations (7)-(9).

Aggregate Casing Wear

Figure 9:
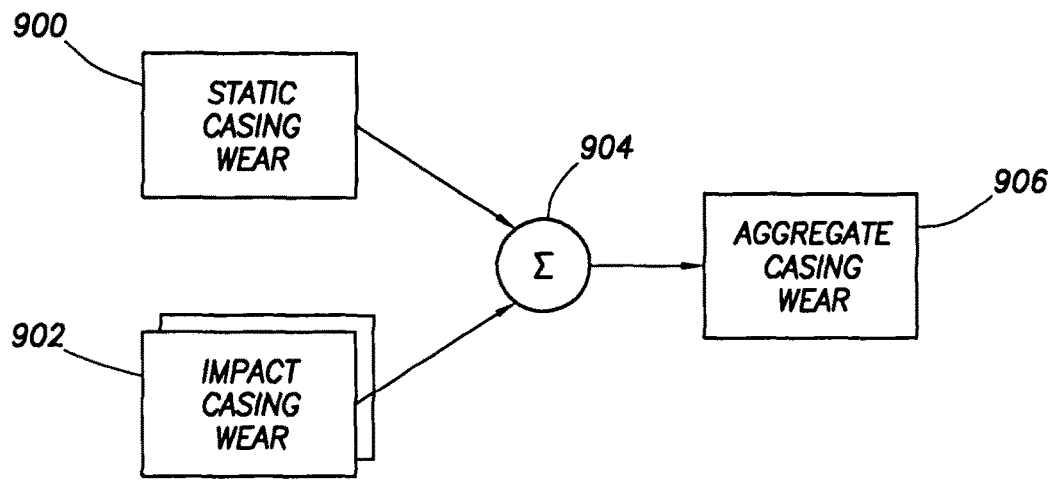
FIG. 9 is a block diagram that shows conceptually combining values of static casing wear and values of impact casing wear to arrive at values of aggregate casing wear in accordance with at least some embodiments.

FIG. 9 shows, in block diagram form, the conceptual creation of a value of aggregate casing wear in accordance with example methods and systems. In particular, for each interval over the course of drilling, a value of static casing wear is determined for periods of time when static casing wear is taking place (block 900). Likewise, for each interval over the course of drilling, a value of impact casing wear is determined for periods of time when impact casing wear is taking place (block 902). It follows that the value of aggregate casing wear (block 906) for any particular interval of the casing is the combination or summation (block 904) of the static casing wear for that interval of the casing and the impact casing wear for that interval of the casing.

In some example systems, a single model for impact casing wear is selected from the plurality of models, thereby creating a selected model. During periods of time when the casing is experiencing impact casing wear, the selected model is used to calculate the value of impact casing wear. It is noted that the selected model used to calculate the impact casing wear need not be the same for each interval of the casing. In a first portion of the casing (e.g., bend 260) a first model may be used, and in a second portion of the casing at a different depth than first portion (e.g., straight section 262) a second model (distinct from the first model) may be used.

Further, impact casing wear at any particular interval of the casing may have a cross-sectional wear pattern that can be considered to be a combination of the various example wear models. Thus, in arriving at a value of impact casing wear, the volume of casing wear may be estimated by two or more different models, and then combined in any suitable fashion. The idea of using two or more models together to arrive at a value of impact casing wear is illustrated by the multiple blocks 902 in FIG. 9. Considering the situation of combining the estimates of impact casing wear from all four example models, the values of casing wear may be combined based on weighting factors. For example, Equation (10) below shows an example mathematical expression for arriving at the value of impact casing wear based on a plurality of underlying models.

$$V_{impact} = \beta V_{parabolic} + \psi V_{elliptical} + \eta V_{cosine} + \lambda V_{skewed} \quad (10)$$

where $V_{parabolic}$ is the calculated volume of casing wear under the parabolic model, $\beta$ is the weighting factor for the parabolic model, $V_{elliptical}$ is the calculated volume of casing wear under the elliptical model, $\psi$ is the weighting factor for the elliptical model, $V_{cosine}$ is the calculated volume of casing wear under the cosine model, $\eta$ is the weighting factor for the cosine model, $V_{skewed}$ is the calculated volume of casing wear under the skewed model, and $\lambda$ is the weighting factor for the skewed model. The values of impact casing wear may be summed in real time, and or may be calculated in real time and then summed at a later time (e.g., when the drilling string is next tripped).

Equation (10) shall not be read to require use of all four example models. In the example systems using multiple impact casing wear models, two or more such models may be used with their weighting factors adjusted accordingly.

Figure 10:
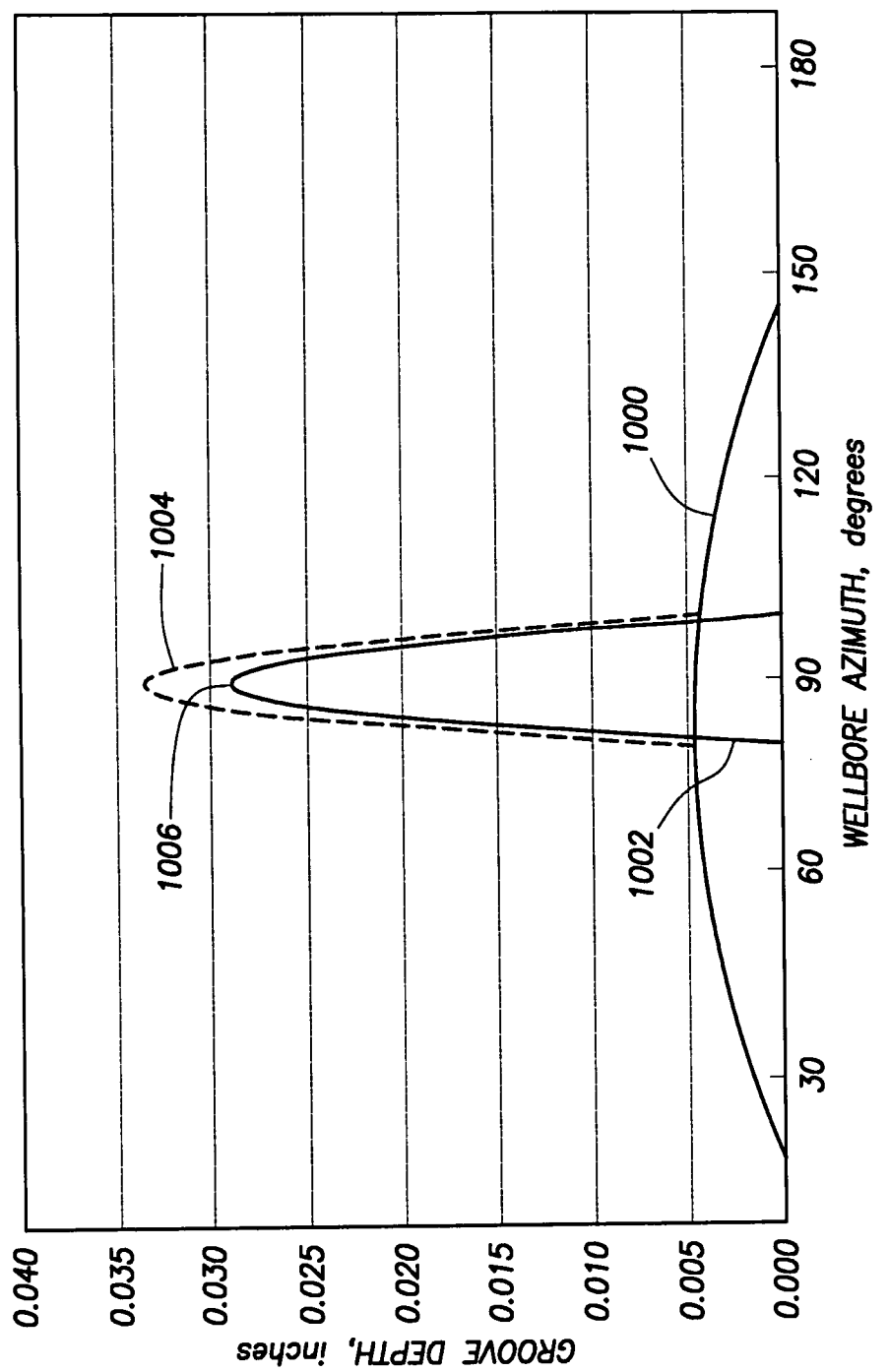
FIG. 10 is a plot that shows static casing wear, impact casing wear, and aggregate casing wear in accordance with at least some embodiments.

In some example systems, the value of aggregate casing wear is considered under a "worst case scenario" in terms of remaining wall thickness of the casing in any particular interval of the casing. Consider, as an example, an interval of the casing that experiences the impact casing wear for an initial period of time, and then experiences static casing wear for the remaining period of time. In the example situation, the casing wear will be the "worst case" in terms of wall thickness remaining in the casing. FIG. 10 shows an example plot of casing groove depth (directly related to remaining wall thickness) against static casing wear and impact casing wear as a function of wellbore azimuth, with the impact casing wear having the example parabolic cross-sectional wear pattern. In particular, line 1000 shows the groove depth for the example parabolic cross-sectional wear pattern considered alone. Line 1002 shows the groove depth for the static casing wear considered alone. However, in the example situation of impact casing wear occurring first, the static casing wear removes volume of casing starting at the already thinned wall thickness caused by the impact casing wear. Thus, the static casing wear considered with the impact casing wear in the example situation results in a greater total groove depth (illustrated by dashed line 1004) than the static casing wear considered alone. The same effect of the interaction of the static and impact casing wear may be experienced with respect to all the example cross-sectional wear modes. However, plots similar to that of FIG. 10 are not produced for each cross-sectional wear mode so as not to further complicate the discussion.

In example systems, a value of groove depth (or relatedly remaining wall thickness) may be estimated from the value of aggregate casing wear. In some systems, the value of groove depth may be estimated using the "worst case" additive nature of the casing wear as discussed with respect to FIG. 10. However, in other example systems, for each interval of the casing, the relative timing of impact casing wear and the static casing wear is taken into consideration. Consider the opposite situation than that discussed with respect to FIG. 10 regarding timing of static and impact casing wear. That is, consider an example where the static casing wear occurs in a first period of time for a particular interval of casing under consideration, and then that impact casing wear takes place in a second period of time for the particular interval. In the example scenario, the deepest groove depth may not be fully additive as shown by line 1004 in FIG. 10. In fact, in the second example scenario the deepest groove depth may be more likely to be the "peak" 1006 of the static casing wear of line 1002. Thought of equivalently, but in terms of volume rather than groove depth, if some static casing wear takes place prior to impact casing wear, the actual volume of impact casing wear may be reduced (by a portion already removed by the static casing wear).

The likelihood of an interval of casing serially experiencing static and then impact casing wear, or experiencing only impact casing wear and then static casing wear, is low. In many cases the wear mode experienced by an interval of casing may switch between the modes with time. For example, an interval may initially experience static casing wear, followed by impact casing wear, again static casing wear, and so on. Thus, in accordance with at least some embodiments the value of aggregate casing wear (and any groove depth or wall thickness estimated based thereon) may take into consideration the timing and pattern of the static casing wear relative to the impact casing wear. The value of impact casing wear may be reduced when significant static casing wear takes place prior to periods of impact casing wear. The specification now turns to an explanation of determining where in the casing static and/or impact casing wear may take place.

Vibration and Force Magnitudes

Software-Based Determinations

In accordance with example systems, the locations within a drilling operation where vibration of the drill string (resulting in impact casing wear) takes place, as well as the rotational speeds of the drill string that cause such vibration, may be determined by any of a variety of well planning tools. For example, WELLPLAN™ brand software available from Landmark Graphics Corporation (Houston, Tex.) enables a drilling engineer to determine the magnitude and location of vibration as a function of rotational speed of a drill string. The WELLPLAN™ brand software may take into account various attributes of the drill string, such as type of piping that makes up the drilling string, and the type and number of tools that constitute the bottomhole assembly 100. Moreover, the WELLPLAN™ brand software may also predict the locations of the vibration within the casing taking into account the geometry of the wellbore. Other software tools, such as the DS WELL ENGINEERING™ brand software also available from Landmark Graphics Corporation may predict the normal force of interaction between the drill string and any particular interval of the casing.

The various example systems may be used in real-time with a drilling operation (such as FIG. 2). However, the various example systems may also be used as a planning tool during the well planning stages to estimate a value of aggregate casing wear to determine whether the planned geometries, drilling parameters, and expected casing thicknesses will remain within tolerances during drilling.

Measured Vibration

In addition to or in place of the locations and magnitudes of vibration that may be supplied from the example WELLPLAN™ and DS WELL ENGINEERING™ brands of software, in other embodiments the location and magnitude of the vibration causing impact wear may be based on measurement by sensors disposed within the drill string. Returning briefly to FIG. 2, the bottomhole assembly 100 may comprise a MWD tool 290 that measures downhole vibration associated with the bottomhole assembly 100. The values of the vibration experienced downhole may be telemetered to the surface in any suitable fashion (e.g., mud pulse telemetry, electromagnetic radiation, acoustic signals in the drill string, or combinations). Computer systems at the surface may then use the indications of downhole vibrations (or the lack thereof) to determine the value of aggregate casing wear at appropriate intervals of the casing. That is, the indications of bottomhole vibration may be used to determine whether static casing wear is taking place (during low or no vibration periods) or whether impact casing wear is taking place. In the situation of the vibration of the bottomhole assembly 100, determinations of aggregate casing wear for intervals of the casing near the distal end of the casing are more likely to utilize the indications of bottomhole assembly 100 vibration.

Figure 11:
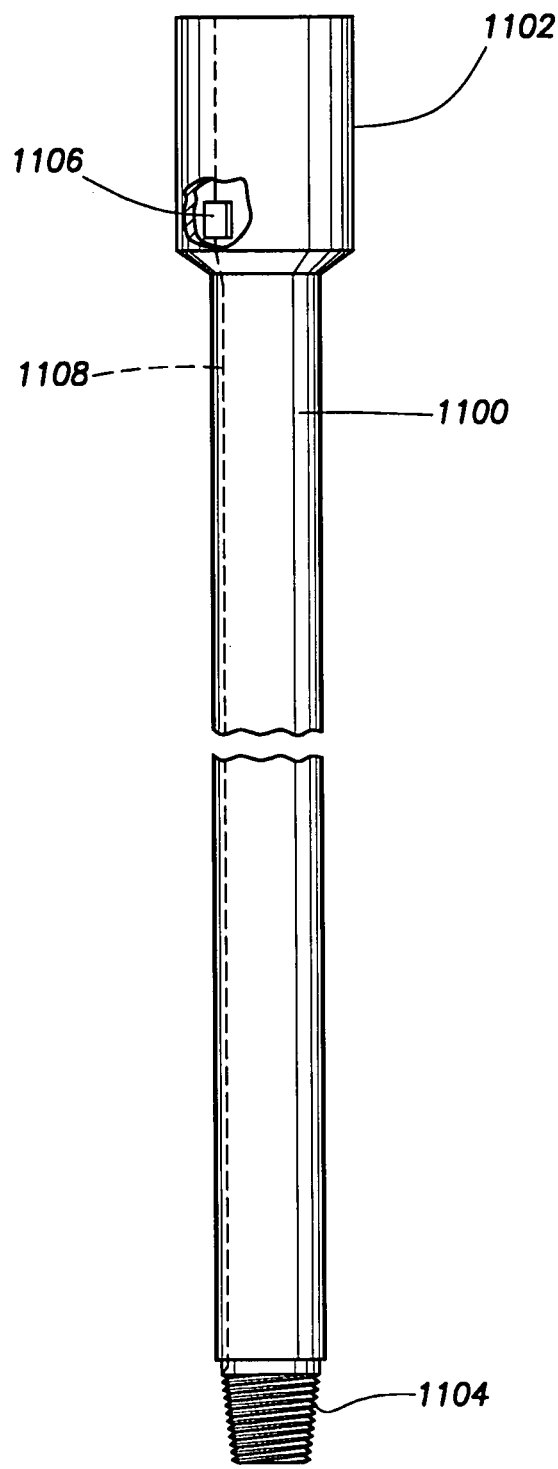
FIG. 11 is a side elevation view that shows a drill pipe in accordance with at least some embodiments.

However, as mentioned above, casing wear may take place at any location along the drill string 104. In yet still further embodiments the drill string itself may comprise vibration sensors measuring vibration of the drill string during drilling, and the vibration information may be sent to the surface in real-time. FIG. 11 shows a side elevation view of a drill pipe 1100 in accordance with example embodiments. In particular, FIG. 11 shows the box end 1102 and the pin end 1104. Embedded with the drill pipe 1100 is vibration sensor 1106 (shown in partial cutaway). While the example sensor 1106 is shown embedded in the box end, the sensor may be placed at any suitable location along the drill pipe 1100. The sensor couples to a communication pathway 1108 also embedded in the drill pipe 1100 (and thus shown in dashed lines), where the communication pathway may extend the length of the drill pipe 1100 such that respective sensors in drill pipes above and below example drill pipe 1100 may also be coupled to the communication pathway 1108. The sensor 1106 may receive operational power from the communication pathway 1108, and also may communicate vibration readings to the surface over the communication pathway 1108.

The sensors (including sensor 1106) may take any suitable form for measuring vibration associated with the drill string. For example, in some cases the communication pathway 1108 is an electrical communication pathway, and the sensors (including sensor 1106) may draw power electrically and communicate electrically. In other example cases, the communication pathway 1108 is an optical communication pathway, and the sensors (including sensor 1106) may draw optical power from the pathway 1108 and communicate optically.

Regardless of the precise physical structure of the sensors in the drill pipes, the further example systems may determine the aggregate casing wear based on the real-time vibration data. For example, for a particular interval of the casing (such as in straight section 262), for a tool joint at the interval, if the vibration sensor shows no vibration (or vibration below a predetermined threshold indicating that the tool joint is staying in "continuous" contact), a value of static casing wear may be determined (and the value of impact casing wear during the same period determined to be zero). For the particular interval again, however, if the vibration sensor shows vibration (or vibration above a predetermined threshold indicating impacts are taking place), a value of impact casing wear may be determined (and the value of static casing wear during the same period determined to be zero). Further still, the sensors may also provide indications of impact force, and thus the $F_{max}$ value in the equations above may be selected based on the impact force sensed by the sensors. It follows that for each interval of the casing the determination of the aggregate casing wear may be based on the vibration sensed by a sensor in or near a tool joint interacting with the respective interval of the casing.

Adjusting the Model

In spite of the best efforts of the well planning software (with or without the real-time vibration measurement), the actual cross-sectional wear pattern experienced by any particular interval of the casing may not match the impact casing wear model or models used to estimate the impact casing wear. Thus, in yet still further embodiments, the models may be adjusted based on actual measured wall thickness.

Figure 12:
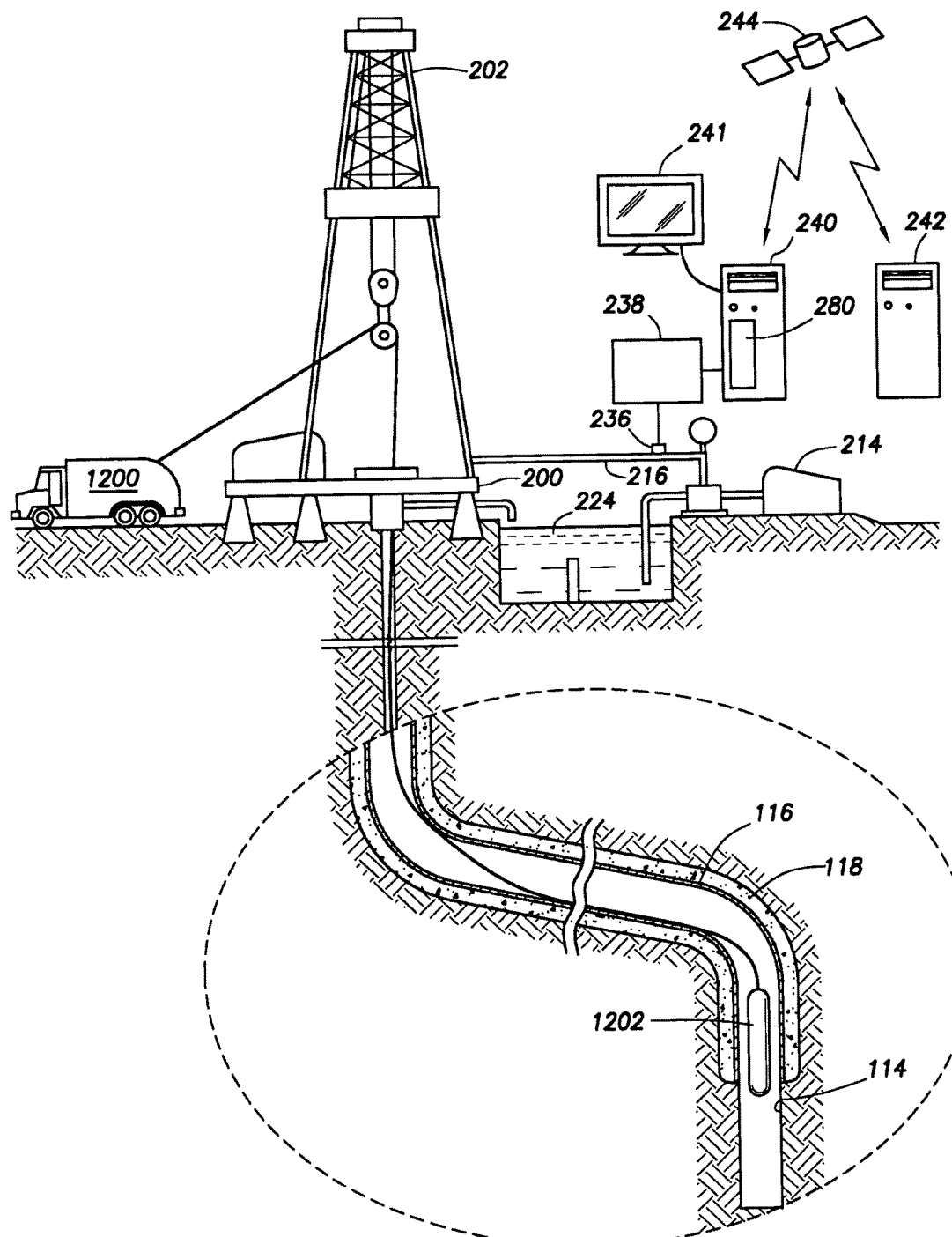
FIG. 12 is a side elevation, partial cross-sectional, view that shows operation of a wireline logging tool in accordance with at least some embodiments.

That is, at certain times during a drilling operation the drill string may be removed or "tripped" to the surface. During periods when the drill string has been removed, various wireline logging tools may be run in the borehole to measure a host of parameters. The wireline logging tool may be a "caliper tool" or a casing wall thickness tool. FIG. 12 shows a situation where the drill string has been removed from the wellbore, and a wireline logging tool run in the wellbore to measure wall thickness. In particular, a logging vehicle 1200 may be used to lower a wireline logging tool 1202 into the borehole 114. In most cases, the logging tool 1202 is lowered to the deepest portion of the borehole 114, and then pulled back to the surface at a steady rate. Logging where the wireline logging tool 1202 performs its function during the downward motion is also possible. The example wireline logging tool 1202 may measure casing wall thickness directly (e.g., based on acoustic signals incident on the casing wall) or may indirectly measure casing wall thickness (e.g., a caliper tools measuring the shape of the inside diameter of the casing).

Regardless of the precise nature of the wireline logging tool, the actual wall thickness at each interval (or oppositely the groove depth) may be determined and compared against the aggregate casing wear for the interval. If the aggregate casing wear and the measured wall thickness differ by a predetermined amount, or differ in cross-sectional wear pattern, the model used to calculate the value of impact casing wear may be adjusted. Adjusting may take many forms. In some cases, a different model may be selected. In other cases, the weighting factor for each model used may be adjusted. In yet still other cases, models may be added and removed from the group of models used to estimate impact casing wear. Further still, various parameters of the models may be adjusted (e.g., normal force, impact time, abrasive wear coefficient, and/or the various values defining the skewed function).

Example Computing Environment

Figure 13:
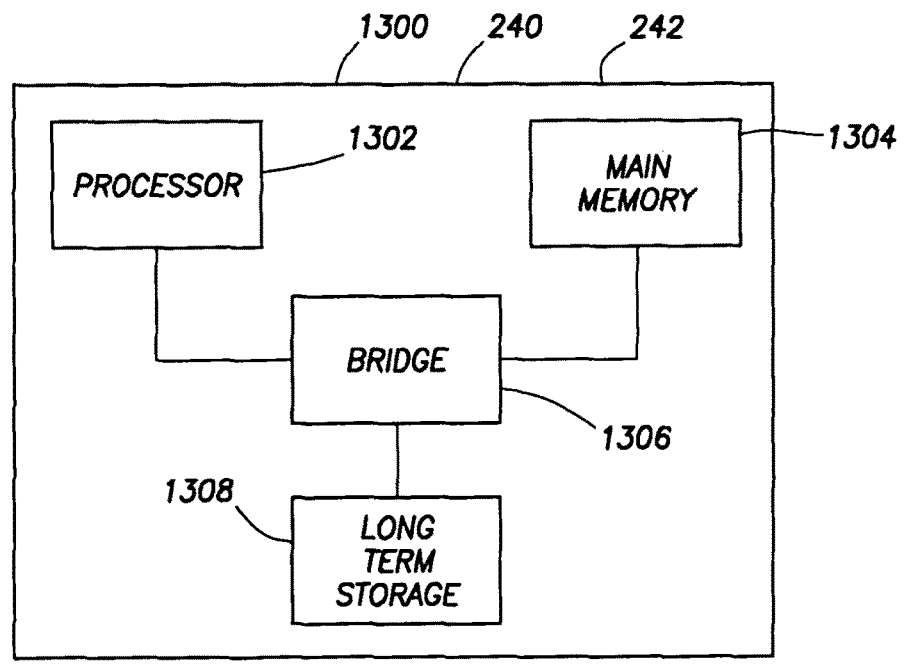
FIG. 13 is a block diagram that shows a computer system in accordance with at least some embodiments.

FIG. 13 shows a computer system 1300, which is illustrative of a computer system upon which any of the various embodiments, or portions thereof, may be practiced. The computer system 1300 may be illustrative of, for example, computer system 240 or 242. In particular, computer system 1300 comprises a processor 1302, and the processor couples to a main memory 1304 by way of a bridge device 1306. Moreover, the processor 1302 may couple to a long term storage device 1308 (e.g., a hard drive, solid state disk, memory stick, optical disc) by way of the bridge device 1306. Programs executable by the processor 1302 may be stored on the storage device 1308, and accessed when needed by the processor 1302. The programs stored on the storage device 1308 may comprise programs to implement the various embodiments of the present specification, such as estimating aggregate values of casing wear. In some cases, the programs are copied from the storage device 1308 to the main memory 1304, and the programs are executed from the main memory 1304. Thus, the main memory 1304, and storage device 1308 shall be considered computer-readable storage mediums.

Figure 14:
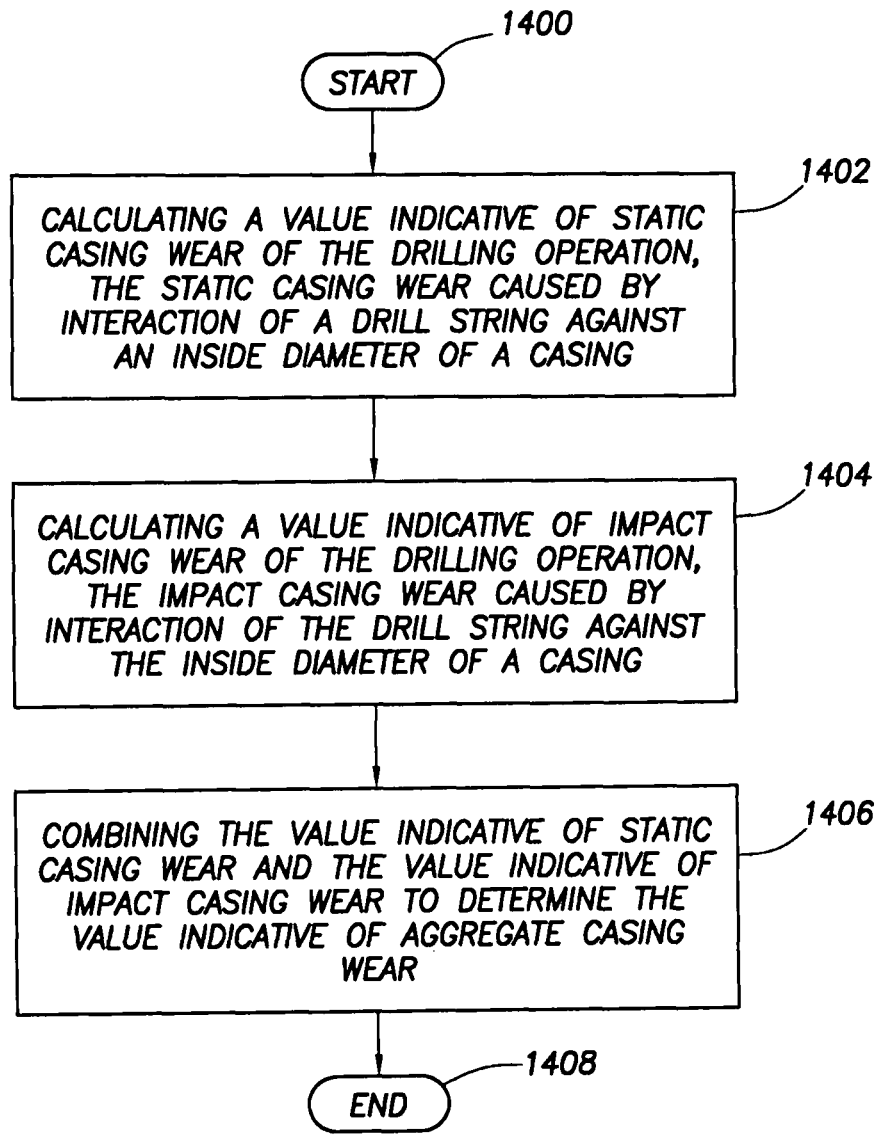
FIG. 14 is a block diagram that shows a method in accordance with at least some embodiments.

FIG. 14 shows a method (some of which may be executed by software) in accordance with example embodiments. In particular, the method may start (block 1400) and comprise: calculating a value indicative of static casing wear of the drilling operation, the static casing wear caused by interaction of a drill string against an inside diameter of a casing (block 1402); calculating a value indicative of impact casing wear of the drilling operation, the impact casing wear caused by interaction of the drill string against the inside diameter of a casing (block 1404); and combining the value indicative of static casing wear and the value indicative of impact casing wear to determine the value indicative of aggregate casing wear (block 1406). Thereafter, the method may end (block 1408), possibly to be restarted, or calculated for a different interval of the casing.

It is noted that while theoretically possible to perform some or all the calculations regarding static and impact casing wear by a human using only pencil and paper, the time measurements for human-based performance of such tasks over all the intervals of the casing in a drilling operation may range from man-years to man-decades, if not more. Thus, this paragraph shall serve as support for any claim limitation now existing, or later added, setting forth that the period of time to perform any task described herein less than the time required to perform the task by hand, less than half the time to perform the task by hand, and less than one quarter of the time to perform the task by hand, where "by hand" shall refer to performing the work using exclusively pencil and paper.

From the description provided herein, those skilled in the art are readily able to combine the methods described above in the form of software with appropriate general purpose or special purpose computer hardware to create a computer system and/or computer subcomponents embodying the invention, to create a computer system and/or computer subcomponents for carrying out the method of the invention, and/or to create a non-transitory computer-readable media (i.e., not a carrier wave) for storing a software program to implement the method aspects of the invention.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The following table provides a method in accordance with example embodiments.

TABLE 1

1. A method of determining a value indicative of aggregate casing wear in a drilling operation, the determining comprising:
    calculating a value indicative of static casing wear of the drilling operation, the static casing wear caused by interaction of a drill string against an inside diameter of a casing;
    calculating a value indicative of impact casing wear of the drilling operation, the impact casing wear caused by interaction of the drill string against the inside diameter of the casing; and
    combining the value indicative of static casing wear and the value indicative of impact casing wear to determine the value indicative of aggregate casing wear.
2. The method of claim 1 wherein calculating the value indicative of impact casing wear further comprises:
    selecting a model from a plurality of models, each model based on a respective cross-sectional wear pattern, the selecting creates a selected model; and
    calculating the value indicative of impact casing wear based on the selected model.

TABLE 1-continued

3. The method of claim 2 wherein selecting the model further comprises:
selecting a first model for use with respect to a first portion of the casing;
selecting a second model for use with respect to a second portion of the casing, the second model distinct from the first model, and the second portion of the casing at a different depth that the first portion of the casing.
4. The method of claim 2 wherein selecting the model further comprises:
selecting a first model which creates a first value; and
selecting a second model which creates a second value, the second model distinct from the first model;
wherein calculating the value indicative of impact casing wear further comprises combining the first and second values.
5. The method of claim 2 wherein selecting a model from the plurality of models further comprises selecting at least one from the group consisting of: a model based on a parabolic cross-sectional wear pattern; a model based on an elliptical cross-sectional wear pattern; a model based on a sinusoidal cross-sectional wear pattern; a model based on a pattern where a single wear peak is offset radially from a static wear peak.
6. The method of claim 1 wherein calculating the value indicative of impact casing wear further comprises:
sensing vibration of a portion of the drill string based on sensors disposed within the drill string;
wherein calculating the value indicative of impact casing wear further comprises calculating the value indicative of impact casing wear based on the vibration sensed by the sensors.
7. The method of claim 6 wherein calculating the value indicative of impact casing wear further comprises at least one selected from the group consisting of: calculating based on an impact force sensed by the sensors; calculating a non-zero value indicative of impact casing wear in locations along the drill string where vibration is sensed; and calculating a zero value indicative of impact casing wear in locations along the drill string where no vibration is sensed.
8. The method of claim 1 further comprising changing a drilling parameter responsive to the value indicative of aggregate casing wear.
9. The method of claim 8 wherein changing the drilling parameter further comprises changing at least one selected from the group consisting of: weight-on-bit; rotational speed of the drill string; and a component of a bottomhole assembly.
10. The method of claim 1 further comprising:
removing the drill string from the casing;
measuring wall thickness of the casing using a wireline logging tool; and
adjusting a model used to calculate the value indicative of impact casing wear, the adjusting based on the wall thickness of the casing.
11. The method of claim 1 wherein calculating the values indicative of static casing wear and impact casing wear further comprises at least one selected from the group consisting of: calculating during planning of a wellbore prior to the drilling operation; and calculating during the drilling operation.

This table shall serve as the basis for post-filing claim amendments.

The following table provides a system in accordance with example embodiments.

TABLE 2

12. A system comprising:
a processor;
a memory coupled to the processor;
the memory storing a program that, when executed by the processor, causes the processor to:
calculate a value indicative of static casing wear for an interval of casing of a drilling operation, the static casing wear based on interaction of a drill string against an inside diameter of the interval of casing;
calculate a value indicative of impact casing wear for the interval of casing of the drilling operation, the impact casing wear based on interaction of the drill string against the inside diameter of the interval of casing; and
combine the value indicative of static casing wear and the value indicative of impact casing wear to determine a value indicative of aggregate casing wear for the interval of casing.
13. The system of claim 12 further comprising:
wherein when the processor calculates the value indicative of static casing wear, the program causes the processor to calculate a plurality of values indicative static casing wear, each value at a respective for the interval of casing;
wherein when the processor calculates the value indicative of impact casing wear, the program causes the processor to calculate a plurality of TABLE 2-continued values indicative impact casing wear, each value at a respective for the interval of casing; and
wherein when the processor combines, the program causes the processor to combine the values at respective for the interval of casing to generate a plurality of values indicative of aggregate casing wear, each value of aggregate casing wear at a respective for the interval of casing.

14. The system of claim 12 wherein when the program calculates the value indicative of impact casing wear, the program further causes the processor to:
select a model from a plurality of models, each model based on a respective cross-sectional wear pattern, the selecting creates a selected model; and
calculate the value indicative of impact casing wear based on the selected model.

15. The system of claim 14 wherein when the processor selects the model, the program further causes the processor to:
select a first model for use with respect to a first interval of casing;
select a second model for use with respect to a second interval of casing, the second model distinct from the first model, the second interval of casing at a different distance along the wellbore than the first interval of casing.

16. The system of claim 14 wherein when the processor selects the model, the program causes the processor to:
select a first model which creates a first value; and
select a second model which creates a second value, the second model distinct from the first model;
calculate the value indicative of impact casing wear further based on a combination of the first and second values.

17. The system of claim 14 wherein when the processor selects the model, the program causes the processor to select at least one from the group consisting of: a model based on a parabolic cross-sectional wear pattern; a model based on an elliptical cross-sectional wear pattern; a model based on a sinusoidal cross-sectional wear pattern; a model based on a pattern where a single wear peak is offset radially from a static wear peak.

18. The system of claim 12:
wherein when the processor calculates the value indicative of impact casing wear, the program further causes the processor to receive an indication of vibration of a portion of the drill string, the indication of vibration based on sensors disposed within the drill string; and
wherein when the processor calculates the value indicative of impact casing wear the program causes the processor to calculate the value indicative of impact casing wear based on the vibration sensed by the sensors.

19. The system of claim 12 wherein the program further causes the processor to perform at least one action selected from the group consisting of: change a drilling parameter during drilling, the change responsive to the value indicative of aggregate casing wear; change a parameter associated with a planned wellbore based on the value indicative of aggregate casing wear; and display on a display device during drilling the value indicative of aggregate casing wear.

20. The system of claim 12 wherein the program further causes the processor to:
receive an indication of casing wall thickness measured by a wireline logging tool; and
adjust a model used to calculate the value indicative of impact casing wear, the adjusting based on the wall thickness of the casing.

21. The system of claim 12 wherein when the processor calculates the values indicative of static casing wear and impact casing wear, the program causes the processor to at least one selected from the group consisting of: calculate during planning of a wellbore prior to the drilling operation; and calculate during the drilling operation.

This table shall serve as the basis for post-filing claim amendments.

The following table provides a system in accordance with example embodiments.

TABLE 3

22. A non-transitory computer-readable medium storing a program that, when executed by a processor, causes the processor to
calculate a value indicative of static casing wear of a drilling operation, the static casing wear based on interaction of a drill string against an inside diameter of a casing;
calculate a value indicative of impact casing wear of the drilling operation, the impact casing wear based on interaction of the drill string against the inside diameter of the casing; and
combine the value indicative of static casing wear and the value indicative of impact casing wear to determine a value indicative of aggregate casing wear.

TABLE 3-continued

23. The non-transitory computer-readable medium of claim 22 further comprising:
wherein when the processor calculates the value indicative of static casing wear, the program causes the processor to calculate a plurality of values indicative static casing wear, each value at a respective distance along wellbore;
wherein when the processor calculates the value indicative of impact casing wear, the program causes the processor to calculate a plurality of values indicative impact casing wear, each value at a respective distance along wellbore; and
wherein when the processor combines, the program causes the processor to combine the values at respective distances along the wellbore to generate a plurality of values indicative of aggregate casing wear, each value of aggregate casing wear at a respective distance along the wellbore.
24. The non-transitory computer-readable medium of claim 22 wherein when the program calculates the value indicative of impact casing wear, the program further causes the processor to:
select a model from a plurality of models, each model based on a respective cross-sectional wear pattern, the selecting creates a selected model; and
calculate the value indicative of impact casing wear based on the selected model.
25. The non-transitory computer-readable medium of claim 24 wherein when the processor selects the model, the program further causes the processor to:
select a first model for use with respect to a first portion of the casing;
select a second model for use with respect to a second portion of the casing, the second model distinct from the first model, the second portion of the casing at a different distance along the wellbore than the first portion of the casing.
26. The non-transitory computer-readable medium of claim 24 wherein when the processor selects the model, the program causes the processor to:
select a first model which creates a first value; and
select a second model which creates a second value, the second model distinct from the first model;
calculate the value indicative of impact casing wear further based on a combination of the first and second values.
27. The non-transitory computer-readable medium of claim 24 wherein when the processor selects the model, the program causes the processor to select at least one from the group consisting of: a model based on a parabolic cross-sectional wear pattern; a model based on an elliptical cross-sectional wear pattern; a model based on a sinusoidal cross-sectional wear pattern; a model based on a pattern where a single wear peak is offset radially from a static wear peak.
28. The non-transitory computer-readable medium of claim 22:
wherein when the processor calculates the value indicative of impact casing wear, the program further causes the processor to receive an indication of vibration of a portion of the drill string, the indication of vibration based on sensors disposed within the drill string; and
wherein when the processor calculates the value indicative of impact casing wear the program causes the processor to calculate the value indicative of impact casing wear based on the vibration sensed by the sensors.
29. The non-transitory computer-readable medium of claim 22 wherein the program further causes the processor to perform at least one action selected from the group consisting of: change a drilling parameter during drilling, the change responsive to the value indicative of aggregate casing wear; change a parameter associated with a planned wellbore based on the value indicative of aggregate casing wear; and display on a display device during drilling the value indicative of aggregate casing wear.
30. The non-transitory computer-readable medium of claim 22 wherein the program further causes the processor to:
receive an indication of casing wall thickness measured by a wireline logging tool; and
adjust a model used to calculate the value indicative of impact casing wear, the adjusting based on the wall thickness of the casing.
31. The non-transitory computer-readable medium of claim 22 wherein when the processor calculates the values indicative of static casing wear and impact casing wear, the program causes the processor to at least one selected from the group consisting of: calculate during planning of a wellbore prior to the drilling operation; and calculate during the drilling operation.

This table shall serve as the basis for post-filing claim amendments.

What is claimed is:
1. A method of determining casing wear during drilling operations, the method comprising:
receiving, by a computer system from one or more sensors disposed within a drill string, an indication of the drill string's interaction with an inside diameter of a casing during a drilling operation along a first section of a wellbore;

calculating a value indicative of static casing wear caused by interaction of the drill string against the inside diameter of the casing during the drilling operation, based on the received indication;

selecting at least one model from a plurality of models, each model based on a respective cross-sectional wear pattern;

calculating a value indicative of impact casing wear caused by interaction of the drill string against the inside diameter of the casing during the drilling operation, based on the selected model;

combining the value indicative of static casing wear and the value indicative of impact casing wear to determine a value indicative of aggregate casing wear for the first section of the wellbore;

adjusting one or more drilling parameters associated with the drilling operation, based on the value indicative of aggregate casing wear; and performing the drilling operation along a second section of the wellbore according to the one or more adjusted drilling parameters.

2. The method of claim 1, wherein selecting the at least one model comprises:
selecting a first model from the plurality of models for a first portion of the casing corresponding to the first section of the wellbore; and
selecting a second model from the plurality of models for a second portion of the casing corresponding to the second section of the wellbore, wherein the second model is distinct from the first model, and the second portion of the casing is at a different depth than the first portion of the casing.

3. The method of claim 2, wherein calculating the value indicative of impact casing wear based on the selected model comprises:
calculating a first value based on the first model;
calculating a second value based on the second model; and
calculating the value indicative of impact casing wear based on the first and second values.

4. The method of claim 1, wherein the at least one model is selected from the group consisting of: a model based on a parabolic cross-sectional wear pattern; a model based on an elliptical cross-sectional wear pattern; a model based on a sinusoidal cross-sectional wear pattern; and a model based on a pattern where a single wear peak is offset radially from a static wear peak.

5. The method of claim 1, wherein the one or more sensors include vibration sensors for measuring vibration of the drill string during the drilling operation, and calculating the value indicative of impact casing wear comprises:
calculating the value indicative of impact casing wear based on the selected model and the vibration measured by the vibration sensors.

6. The method of claim 5, wherein the value indicative of impact casing wear is at least one of: a value of an impact force of the drill string's interaction with a portion of the casing as a function of time; a non-zero value indicative of impact casing wear in locations along the drill string where vibration is measured by the vibration sensors; or a zero value indicative of impact casing wear in locations along the drill string where no vibration is measured by the vibration sensors.

7. The method of claim 1, wherein the respective values indicative of static casing wear and impact casing wear are calculated during at least one of a planning stage of the drilling operation prior to the drilling of the wellbore or while the wellbore is drilled during the drilling operation.

8. A system comprising:
a processor;
a memory coupled to the processor;
the memory storing a program that, when executed by the processor, causes the processor to:
receive, from one or more sensors disposed within a drill string, an indication of the drill string's interaction with an inside diameter of a casing during a drilling operation along a first section of a wellbore;
calculate a value indicative of static casing wear caused by interaction of the drill string against an inside diameter of an interval of casing during the drilling operation, based on the received indication;
select at least one model from a plurality of models, each model based on a respective cross-sectional wear pattern;
calculate a value indicative of impact casing wear caused by interaction of the drill string against the inside diameter of the interval of casing during the drilling operation, based on the selected model;
combine the value indicative of static casing wear and the value indicative of impact casing wear to determine a value indicative of aggregate casing wear for the interval of casing along the first section of the wellbore;
adjust one or more drilling parameters associated with the drilling operation, based on the value indicative of aggregate casing wear; and
perform the drilling operation by using the drill string to drill a second section of the wellbore according to the one or more adjusted drilling parameters.

9. The system of claim 8, wherein the program, when executed by the processor, further causes the processor to:
calculate a plurality of values indicative static casing wear, each value at a respective for the interval of casing;
calculate a plurality of values indicative impact casing wear, each value at a respective for the interval of casing; and
combine the values at respective for the interval of casing to generate a plurality of values indicative of aggregate casing wear, each value of aggregate casing wear at a respective for the interval of casing.

10. The system of claim 8, wherein the program further causes the processor to:
select a first model from the plurality of models for use with respect to a first interval of casing corresponding to the first section of the wellbore; and
select a second model from the plurality of models for use with respect to a second interval of casing corresponding to the second section of the wellbore, wherein the second model is distinct from the first model, and the second interval of casing is at a different distance along the wellbore than the first interval of casing.

11. The system of claim 10, wherein the program further causes the processor to:
calculate a first value based on the first model;
calculate a second value based on the second model; and
calculate the value indicative of impact casing wear based on a combination of the first and second values.

12. The system of claim 8, wherein the at least one model is selected from the group consisting of: a model based on a parabolic cross-sectional wear pattern; a model based on an elliptical cross-sectional wear pattern; a model based on a sinusoidal cross-sectional wear pattern; and a model based on a pattern where a single wear peak is offset radially from a static wear peak.

13. A non-transitory computer-readable medium storing a program that, when executed by a processor, causes the processor to:
    receive, from one or more sensors disposed within a drill string, an indication of the drill string's interaction with an inside diameter of a casing during a drilling operation along a first section of a wellbore;
    calculate a value indicative of static casing wear caused by interaction of the drill string against an inside diameter of a casing during the drilling operation, based on the received indication;
    select at least one model from a plurality of models, each model based on a respective cross-sectional wear pattern;
    calculate a value indicative of impact casing wear caused by interaction of the drill string against the inside diameter of the casing during the drilling operation, based on the selected model;
    combine the value indicative of static casing wear and the value indicative of impact casing wear to determine a value indicative of aggregate casing wear along the first section of the wellbore;
    adjust one or more drilling parameters associated with the drilling operation, based on the value indicative of aggregate casing wear; and
    perform the drilling operation along a second section of the wellbore according to the one or more adjusted drilling parameters.

14. The non-transitory computer-readable medium of claim 13, wherein the program further causes the processor to:
    calculate a plurality of values indicative static casing wear, each value at a respective distance along the wellbore;
    calculate a plurality of values indicative impact casing wear, each value at a respective distance along the wellbore; and
    combine the values at respective distances along the wellbore to generate a plurality of values indicative of aggregate casing wear, each value of aggregate casing wear at a respective distance along the wellbore.

15. The non-transitory computer-readable medium of claim 13, wherein the program further causes the processor to:
    select a first model from the plurality of models for use with respect to a first portion of the casing corresponding to the first section of the wellbore;
    select a second model from the plurality of models for use with respect to a second portion of the casing corresponding to the second section of the wellbore, wherein the second model is distinct from the first model, and the second portion of the casing is at a different distance along the wellbore than the first portion of the casing.

16. The non-transitory computer-readable medium of claim 15, wherein the program further causes the processor to:
    calculate a first value based on the first model;
    calculate a second value based on the second model; and
    calculate the value indicative of impact casing wear based on a combination of the first and second values.

17. The non-transitory computer-readable medium of claim 13, wherein the at least one model is selected from the group consisting of: a model based on a parabolic cross-sectional wear pattern; a model based on an elliptical cross-sectional wear pattern; a model based on a sinusoidal cross-sectional wear pattern; and a model based on a pattern where a single wear peak is offset radially from a static wear peak.

* * * * *